United States Patent [19]

Weiner et al.

[11] Patent Number: 5,639,598

[45] Date of Patent: Jun. 17, 1997

[54] METHOD AND KIT FOR IDENTIFICATION OF ANTIVIRAL AGENTS CAPABLE OF ABROGATING HIV VPR-RIP-1 BINDING INTERACTIONS

[75] Inventors: David B. Weiner, Merion, Pa.; Yosef Refaeli, Boston, Mass.; David N. Levy, Birmingham, Ala.

[73] Assignee: The Trustees of the University of Pennsylvania, Philadelphia, Pa.

[21] Appl. No.: 246,177

[22] Filed: May 19, 1994

[51] Int. Cl.$^6$ .................... C12Q 1/70; G01N 33/53
[52] U.S. Cl. .................................. 435/5; 435/7.1
[58] Field of Search ................ 514/1; 435/5, 7.8, 435/7.1; 530/387, 388.22, 388.35

[56] References Cited

U.S. PATENT DOCUMENTS

| | | | |
|---|---|---|---|
| 4,296,206 | 10/1981 | Simons, Jr. .................. | 435/240 |
| 4,386,085 | 5/1983 | Teutsch et al. ............... | 424/238 |
| 4,447,424 | 5/1984 | Teutsch et al. ............... | 424/238 |
| 4,477,445 | 10/1984 | Philibert et al. .............. | 424/239 |
| 4,519,946 | 5/1985 | Teutsch et al. .......... | 260/239.55 R |
| 4,540,686 | 9/1985 | Philibert et al. .............. | 514/179 |
| 4,547,493 | 10/1985 | Teutsch et al. ............... | 514/179 |
| 4,634,695 | 1/1987 | Torelli et al. ................. | 514/178 |
| 4,634,696 | 1/1987 | Teutsch et al. ............... | 514/179 |
| 4,753,932 | 6/1988 | Teutsch et al. ............... | 514/179 |
| 4,774,236 | 9/1988 | Cook et al. .................. | 514/176 |
| 4,814,327 | 3/1989 | Ottow et al. .................. | 514/179 |
| 4,829,060 | 5/1989 | Ottow et al. .................. | 514/179 |
| 4,861,763 | 8/1989 | Cook et al. .................. | 514/172 |
| 4,912,097 | 3/1990 | Teutsch et al. ............... | 514/172 |
| 4,943,566 | 7/1990 | Nedelec et al. ............... | 514/179 |
| 4,954,490 | 9/1990 | Cook et al. .................. | 514/176 |
| 4,978,657 | 12/1990 | Teutsch et al. ............... | 514/175 |
| 5,006,518 | 4/1991 | Moguilewsky et al. ........ | 514/179 |
| 5,011,829 | 4/1991 | Hirsch et al. ................. | 514/50 |
| 5,043,322 | 8/1991 | Teutsch et al. ............... | 514/173 |
| 5,064,822 | 11/1991 | Philibert et al. .............. | 514/172 |
| 5,073,548 | 12/1991 | Cook et al. .................. | 514/169 |
| 5,089,488 | 2/1992 | Ottow et al. .................. | 514/179 |
| 5,089,635 | 2/1992 | Neff et al. .................... | 549/297 |
| 5,093,507 | 3/1992 | Scheidges et al. ............ | 552/523 |
| 5,095,010 | 3/1992 | Elger et al. ................... | 514/171 |
| 5,095,129 | 3/1992 | Ottow et al. .................. | 552/510 |
| 5,132,299 | 7/1992 | Ottow et al. .................. | 514/169 |
| 5,166,146 | 11/1992 | Moguilewsky et al. ........ | 514/179 |
| 5,276,023 | 1/1994 | Moguilewsky et al. ........ | 514/179 |
| 5,298,429 | 3/1994 | Evans et al. .................. | 436/501 |
| 5,436,128 | 7/1995 | Harpold et al. ............... | 435/6 |

OTHER PUBLICATIONS

Rogel et al., 1995, J. Virol. 69:882–888.
Zhao et al., 1994, J. Biol. Chem. 269:15577–15582.
Evans, R., 1988, Science 240 889–895.
Beato, M., 1989, Cell 56:335–344.
Storrie and Madden, 1990, Methods Enzymol. 182:203–225.
Levy, J., 1993, Microbiol. Rev. 57:183–289.
Holland et al., 1992, Curr. Topics Microbiol. Immunol. 176:1–20.

Heinzinger, N. et al., "The Vpr Protein of Human Immunodeficiency Virus Type 1 Influences Nuclear Localization of Viral Nucleic Acids in Nondividing Host Cells", PNAS USA 1994, 91, 7311–7315.

Refaeli, Y. et al., "The Glucocorticoid Receptor Type II Complex is Target of the HIV–1 Vpr Gene Product", PNAS USA 1995, 92, 3621–3625.

Zhao et al., "Biochemical Mechanism of HIV–1 Vpr Function", Journal of Biological Chemistry 269:15577–15582.

Valentin, et al. "In Vitro Maturation of Mononuclear Phagocytes And Susceptibility to HIV–1 Infection" J. AIDS 4:751–759 (1991).

Granner et al. [80] "Tyrosine Aminotransferase (Rat Liver)", Meth. Enzymol. 15:633–637 (1970).

Lefkowitz et al. "Isolation of Lymphocytopathic Retroviruses From San Francisco Patients With AIDS", Science 225:840–842 (1984).

Roulston et al. "Induction of Monocytic Differentiation And NF–κB–like Activities By Human Immundeficiency Virus 1 Infection Of Myelomonoblastic Cells", J. Exp. Med. 175:751–763 (1992).

Ogawa et al. "Mutational Analysis Of The Human Immunodeficiency Virus vpr Open Reading Frame", J. Virol. 63:4110–4114 (1989).

Dedera et al. "Viral Protein R of Human Immunodeficiency Virus Types 1 and 2 Is Dispensable For Replication And Cytopathogenicity In Lymphoid Cells", J. Virol. 63:3205–3208 (1989).

Levy et al., "Induction Of Cell Differentiation By Human Immunodeficiency Virus 1 vpr", Cell 72:541 (1993).

Rose et al., "Frequent Identification Of HIV–1 DNA In Bronchoalveolar Lavage Cells Obtained From Individuals With The Acquired Immunodeficiency Syndrome", Am. Rev. Respir. Dis. 143:850–854 (1986).

Gallo et al., "Frequent Detection And Isolation of Cytopathic Retroviruses (HTLV–III) Fron Patients With AIDS And At Risk For AIDS", Science 224:500–503 (1984).

(List continued on next page.)

Primary Examiner—Robert D. Budens
Assistant Examiner—Jeffrey S. Parkin
Attorney, Agent, or Firm—Woodcock Washburn Kurtz Mackiewicz & Norris LLP

[57] ABSTRACT

Human and simian immunodeficiency viruses (HIV/SIVs) contain, in addition to the canonical gag/pol/env genes, additional small open reading frames (ORFs) encoding gene products, including the 96-amino acid 15-kDa virion-associated HIV-1 Vpr gene product. Vpr functions as a regulator of cellular processes related to HIV replication. A biologically active recombinant HIV-1 Vpr protein was employed as a ligand to identify its cognate cellular target (s). A novel 41-kDa cytosolic viral protein R interacting protein, designated Rip-1, was identified using the recited assay. Rip-1 displays a wide-tissue distribution, including relevant targets of HIV infection. HIV-1 Vpr induced nuclear translocation of Rip-1. This invention provides novel biochemical reagents and methods that will facilitate the identification of antiviral agents.

9 Claims, No Drawings

OTHER PUBLICATIONS

Griffin et al., "Activation Of HIV Gene Expression During Monocyte Differentiation By Induction Of NF-κB", *Nature* 339:70–73 (1988).

Zack et al., "HIV-1 Production From Infected Peripheral Blood T Cells After HTLV-1 Induced Mitogenic Stimulation", *Science* 240:1026–1029 (1988).

Rich et al., "Increased Susceptibility Of Differentiated Mononuclear Phagocytes To Productive Infection With Human Immunodeficiency Virus-1 (HIV-1)", *J. Clin. Invest.* 89:176–183 (1992).

Schuitemaker et al., "Biological Phenotype Of Human Immunodeficiency Virus Type 1 Clones At Different Stages Of Infection: Progression Of Disease Is Associated With A Shift From Monocytotropic To T-Cell-Tropic Virus Populations", *J. Virol.* 66:1354–1360 (1992).

Shibata et al., "Mutational Analysis Of The Human Immunodeficiency Virus Type 2 (HIV-2) Genome In Relation To HIV-1 and Simian Immunodeficiency Virus SIV", *J. Virol.* 64:742–747 (1990).

Li et al., "Human Immunodeficiency Virus Type 1 DNA Synthesis, Integration, And Efficent Viral Replication In Growth-Arrested T Cells", *J. Virol.* 67:3969–3977.

Chantal-Petit et al., "Human Immunodeficiency Virus Infection Down-Regulates HLA Class II Expression And Induces Differentiation In Promonocytic U937 Cells", *J. Clin. Invest.* 79:1883–1889 (1987).

Cohen et al., "Human Immunodeficiency Virus vpr Product Is A Virion-Associated Regulatory Protein", *J. Virol.* 64:3097–3099 (1990).

Westervelt et al., "Dual Regulation Of Silent And Productive Infection In Monocytes By Distinct Human Immunodeficiency Virus Type 1 Determinants", *J. Virol.* 66:3925–3931 (1992).

Yu et al., "Open Reading Frame vpr Of Simian Immunodeficiency Virus Encodes A Virion–Associated Protein", *J. Virol.* 64:5688–5693 (1990).

Hattori et al., "The Human Immunodeficiency Virus Type 2 vpr Gene Is Essential For Productive Infection Of Human Macrophages", *Proc. Natl. Acad. Sci. USA* 87:8080–8084 (1990).

Salahuddin, S.Z. et al., *Blood,* 68:281 (1986).

Myers, G. et al., *AIDS Res. Hum. Retrovir.* 8:373 (1992).

Wong-Staal, F. et al., *AIDS Res. Hum. Retroviruses* 3:33–39 (1987).

Yuan, X. et al., *AIDS Res. Hum. Retroviruses* 6:1265–1271 (1990).

Agarwal, M.K. et al. "Glucocorticoid Antagonists" *FEBS Letters,* 217:221–226 (1987).

Sambrook et al. "Molecular Cloning: A Laboratory Manual", Second Edition *Cold Spring Harbor Press* (1989).

Voller et al., "Immunoassays for the 80's", Eds. *University Park* (1981).

Work, T.S. et al. "Laboratory Techniques And Biochemistry In Molecular Biology", *North Holland Publishing Company,* N.Y. (1978).

Wide, "Radioimmune Assay Method", *Kirkham, Ed., E. & S. Livingstone, Edinburg* pp. 199–206 (1970).

Myers, G., et al., "Human Retroviruses And AIDS, 1991, A Compilation And Analysis Of Nucleic Acid And Amino Acid Sequences", Division of AIDS, National Institute of Allergy and Infectious Diseases, published by *Theoretical Biology and Biophysicis Group,* Los Alamos National Laboratory, Los Alamos NM.

METHOD AND KIT FOR IDENTIFICATION OF ANTIVIRAL AGENTS CAPABLE OF ABROGATING HIV VPR-RIP-1 BINDING INTERACTIONS

CROSS REFERENCE TO RELATED APPLICATIONS

This application is related to U.S. application Ser. No. 08/167,519, filed Dec. 15, 1993, now abandoned, which is incorporated herein by reference in its entirety.

BACKGROUND OF THE INVENTION

1. Field of the Invention

The present invention relates to methods and compositions for treating human immunodeficiency virus (HIV) infected individuals by administering to such individuals, compositions which inhibit or prevent replication of the HIV. In particular, the present invention relates to compositions which inhibit or prevent the replicatire and other essential functions of HIV viral protein R (vpr) by competitively binding to the vpr target in human cells, the vpr binding protein (rip-1). More particularly, the present invention relates to compositions which are glucocorticoid receptor (GR) antagonists, which by binding to rip-1, a GR type molecule, prevent vpr from binding to rip-1, and thereby interfere in the essential activities of the complex necessary for HIV replication. In particular, the antagonist prevents translocation of the vpr/rip-1 complex from the cytosol to the nucleus, or signaling of said translocated complex, whereby vpr would otherwise carry on its various activities essential to replication of HIV. The present invention also relates to methods of identifying such compositions which inhibit or prevent replication of HIV.

2. Brief Description of the Prior Art

One approach to treating individuals infected with HIV is to administer to such individuals compounds which directly intervene in and interfere with the machinery by which HIV replicates itself within human cells. With that approach in mind, it is first noted that HIV is a lentivirus whose genome contains only about 9–11 kb of genetic material and less than 10 open reading frames. Thus, each HIV gene is likely to play a vital role in the natural history of the virus in vivo. Further, HIV possesses a collection of small, positive strand open reading frames which encode 1–2 exon genes whose protein products regulate various aspects of the virus' life cycle. Some of these genes are genetic transactivating factors which are necessary for virus replication in all permissive cell types.

The complexity of HIV can thus be attributed to the intricate patterns of regulation of gene expression observed during the vital lifecycle. Since all such regulatory mechanisms are accomplished by the interaction of virally encoded proteins with distinct host cell factors, it is possible to discover compounds which directly interfere with the binding and translocation of those proteins which are essential to replication of HIV.

The progression from HIV infection to AIDS is in large part determined by the effects of HIV on the cells that it infects, including $CD4^+$ T lymphocytes and macrophages. On the other hand, cell activation, differentiation and proliferation in turn regulate HIV infection and replication in T cells and macrophages. Gallo, R. C. et al. (1984) *Science* 224:500; Levy, J. A. et al., (1984) *Science* 225:840; Zack, J. A. et al. (1988) *Science* 240:1026; Griffin, G. E. et al., (1988) *Nature* 339:70; Valentin, A. et al. (1991) *J. AIDS* 4:751; Rich, E. A. et al., (1992) *J. Clin. Invest.* 89:176; and Schuitemaker, H. et al. (1992) *J. Virol.* 66:1354. Cell division per se may not be required since HIV and other lentiviruses can proliferate in nonproliferating, terminally differentiated macrophages and growth-arrested T lymphocytes. Rose, R. M. et al. (1986) *Am. Rev. Respir. Dis.* 143:850; Salahuddin, S. Z. et al. (1986) *Blood* 68:281; and Li, G. et al. (1993) *J. Virol.* 67:3969. The ability of lentiviruses, including HIV, to replicate in nonproliferating cells, particularly in macrophages, is believed to be unique among retroviruses and it is significant that several lentiviruses contain a vpr-like gene. Myers, G. et al. (1992) *AIDS Res. Hum. Retrovir.* 8:373. HIV infection of myeloid cell lines can result in a more differentiated phenotype and increase the expression of factors such as NF-KB which are necessary for HIV replication. Roulston, A. et al. (1992) *J. Exp. Med.* 175:751; and Chantal Petit, A. J. et al. (1987) *J. Clin. Invest.* 79:1883.

Since the demonstration in 1987 that the small open reading frame within HIV-1 designated R encodes a 15 KD protein (Wong-Staal, F., et al., (1987) *AIDS Res. Hum. Retroviruses* 3:33–39), there has been a growing body of literature regarding the function of the virat protein R (vpr). The vpr open reading frame is conserved within all genomes of HIV-1 and HIV-2 and within all pathogenic isolates of simian immunodeficiency virus (SIV) genomes. The evolutionary requirement for economy in design is deemed to require that the presence of vpr in the HIV genome is related to a specific and non dispensable function in the vital life cycle. Furthermore, the vpr protein is the only HIV-1 regulatory gene product which has been shown to be incorporated into virions. This would normally suggest a structural role for vpr, but since vpr deleted viruses are able to produce normal virions, this is deemed to be further evidence of a regulatory role for this molecule.

Further, the presence of vpr in virions has been associated with increased replication kinetics in T lymphocytes, and with the ability of HIV to establish productive infection in monocytes and macrophages. Thus, it has been reported that mutations in the vpr gene result in a decrease in the replication and cytopathogenicity of HIV-1, HIV-2, and SIV in primary $CD4^+$T lymphocytes and transformed T cell lines. See, e.g., Ogawa, K., et al., (1989) *J. Virol.* 63:4110–4114; Shibata, R., et al. (1990a) *J. Med. Primatol.* 19:217–225; Shibata, R., et al. (1990b) *J. Virol.* 64:742–747 and Westervelt, P. et al. (1992) *J. Virol.* 66:3925, although others have reported that mutated vpr gene had no effect on replication (Dedera, D., et al. (1989) *Virol.* 63:3205–3208).

Importantly, HIV-2 mutated for vpr has been reported unable to infect primary monocyte/macrophages (Hattori, N., et al. (1990) *Proc. Natl. Acad. Sci. U.S.A.* 87:8080–8084). Further, viral replication in macrophages may be almost completely inhibited by antisense ribonucleotides targeting the vpr open reading frame. This, together with the induction of rhabdomyosarcoma cellular differentiation, are deemed to dictate a crucial function for vpr in HIV pathogenesis.

The presence of vpr protein in vital particles means an early function for vpr during the infection process, following virus penetration and uncoating. This role is considered to involve vpr interaction with cellular regulatory mechanisms resulting in an increase in cell permissiveness to sustain viral replication processes. See, e.g., Cohen, E. A., et al. 1990a *J. Virol.* 64:3097–3099; Yu, X. F., et al. (1990) *J. Virol.* 64:5688–5693.; and, Yuan, X., et al., (1990) *AIDS Res. Hum. Retroviruses* 6:1265–1271.

Vpr action can involve the upregulation of cellular elements which enhance viral gene expression, or the downmodulation of cellular inhibitory pathways affecting such vital processes. Such cellular disregulation is consistent with the observation that vpr is sufficient for the differentiation and cessation in cellular proliferation of rhabdomyosarcoma and osteosarcoma cell lines. Thus, the vpr gene of HIV-1 has been shown to induce cellular growth inhibition and differentiation in tumor lines of intermediate differentiation in vitro (Levy, D. N. et al. (1993) *Cell* 72:541). Thus, the ability of a vitally associated protein such as vpr to reinitiate an arrested developmental program is clearly based upon its interaction with other cellular proteins, and since vpr protein originates within viral particles, it is considered that vpr must, accordingly, play a role in establishing productive infection.

In order for vpr to exert its cellular effects, it requires a cellular ligand, which would mediate these functions. There has been no description heretofore of such a ligand, which may also be referred to as a receptor or binding protein, for vpr. Accordingly, there is described herein, as a part of the present invention, the isolation of a 41 KD vpr cytosolic binding protein, rip-1. Vpr and rip-1 coelute in an immunoaffinity system, and can be specifically crosslinked to a 58 KD complex. Using peptide and antibody competition, the site of their interaction has been resolved to amino acids 38 to 60 on the vpr amino acid sequence. Rip-1 has been detected in various cell lines. Rip-1 selectively translocates from the cytosol to the nucleus upon exposure of the cell to vpr either in a soluble form, or through infection with wild type virus, but not in response to PMA, suggesting a coupling in their regulatory functions.

Part of the present invention is the discovery, described in detail further below, of the likelihood that rip-1 is a member of the steroid hormone receptor superfamily, and particularly, that it behaves as a member of the glucocorticoid receptor (GR) family, and more particularly, that it behaves as a GR type II receptor molecule. Thus, it is a key aspect of the present invention to treat individuals infected with HIV, by administering to such individuals compounds which are steroid hormone receptor antagonists, particularly glucocorticoid receptor antagonists, and more particularly GR type II receptor antagonsts. Such receptor antagonists of the present invention will inhibit or prevent the replicatire and other essential functions of vpr by competitively binding to the vpr target in human cells, the vpr binding protein, rip-1.

Perhaps the best known glucocorticoid receptor antagonist is RU-486, or mifepristone. Acting also as a progesterone receptor antagonist, it is a therapeutic abortifacient approved for use in combination with prostaglandins, in Europe and elsewhere. Many other such glucocorticoid receptor antagonists have been described in the literature. While it is possible that RU-486 may have been taken by an individual who was also suffering from an HIV infection at the time, such use would have been purely coincidental, since there has been no suggestion until the present invention that a glucocorticoid receptor antagonist would in any way inhibit or prevent replication of HIV. Moreover, such coincidental use would in all likelihood also have included the concomitant use of prostaglandins, a combination wholly outside the scope of the present invention.

There remains an urgent need to identify methods of treating individuals suffering from HIV infection. There remains a need to identify compounds which prevent or inhibit HIV replication in infected cells and thereby are useful for treating individuals suffering from HIV infection.

SUMMARY OF THE INVENTION

The present invention relates to A method for treating an individual exposed to or infected with HIV comprising administering to said individual a therapeutically effective amount of one or more compounds which inhibit or prevent replication of said HIV by interfering with the replicatire or other essential functions of vpr expressed by said HIV, by competitively binding to the vpr target in human cells, rip-1, so as to interfere in the essential activities of said complex necessary for HIV replication. In particular, the antagonist prevents translocation of the vpr/rip-1 complex from the cytosol of said human cells to the nuclei of said cells, or signaling of said translocated complex, whereby vpr would otherwise carry on activities essential to replication of HIV. Based on rip-1 being a member of the steroid hormone receptor superfamily, and particularly, on its being a member of the glucocorticoid receptor (GR) family, and more particularly, on its being a GR type II receptor molecule, it has been discovered that compounds which are especially effective for this method of treatment are those compounds which are antagonists for the receptors just mentioned.

Particularly therefore, the present invention relates to a method for treating HIV infected individuals by administering to such individuals a therapeutically effective amount of a composition comprising one or more steroid hormone receptor antagonists, preferably glucocorticoid receptor antagonists, more preferably glucocorticoid receptor Type II antagonists, which bind to rip-1, prevent vpr from binding to rip-1, and thereby prevent translocation of the vpr/rip-1 complex from the cytosol to the nuclei of the infected cell, where vpr carries on its various activities essential to replication of HIV.

The present invention also relates to such a method of treating HIV infected individuals as described above, wherein there is coadministered with one or more of said glucocorticoid receptor antagonists, one or more therapeutic agents useful for treating HIV infected individuals, selected from the group consisting of zidovudine (AZT), acyclovir, ganciclovir, foscarnet, interferon alpha-2a, and interferon alpha-2b.

The present invention further relates to a pharmaceutical composition for treatment of an individual exposed to or infected with HIV comprising a therapeutically effective amount of one or more compounds which inhibit or prevent replication of said HIV by interfering with the replicatire or other essential functions of vpr expressed by said HIV, by competitively binding to the vpr target in human cells, rip-1, whereby vpr would otherwise carry on activities essential to replication of HIV; or a pharmaceutically acceptable salt or ester thereof; and a pharmaceutically acceptable carrier therefor.

The present invention also relates to a pharmaceutical composition wherein said compound also prevents translocation of the vpr/rip-1 complex from the cytosol of said human cells to the nuclei of said cells, or signaling of said translocated complex, whereby vpr would otherwise carry on activities essential to replication of HIV.

The present invention further relates to a pharmaceutical composition wherein the compound or compounds which competitively bind to rip-1, or also in addition prevent or inhibit translocation of the vpr/rip-1 complex from the cytosol of said human cells to the nuclei of said cells, or signaling of said translocated complex, is one or more members selected from the group consisting of steroid hormone receptor antagonists, glucocorticoid receptor antagonists, and glucocorticoid receptor Type II antagonists. In particular, the present invention relates to a pharmaceutical composition for treatment of an individual exposed to or infected with HIV comprising a therapeutically effective amount of one or more compounds which are glucocorticoid receptor Type II antagonists, or a pharmaceutically acceptable salt or ester thereof; and a pharmaceutically acceptible carrier therefor.

The present invention also relates to pharmaceutical compositions comprising a therapeutically effective amount of one or more of said glucocorticoid receptor antagonists, together with one or more therapeutic agents useful for treating HIV infected individuals, selected from the group consisting of zidovudine (AZT), acyclovir, ganciclovir, foscarnet, interferon alpha-2a, and interferon alpha-2b, together with a pharmaceutically acceptable carrier.

The present invention further relates to pharmaceutical composition for treatment of an individual exposed to or infected with HIV comprising a therapeutically effective amount of one or more compounds which inhibit or prevent replication of said HIV by interfering with the replicatire or other essential functions of vpr expressed by said HIV, by competitively binding to the vpr target in human cells, rip-1, or additionally preventing translocation of the vpr/rip-1 complex from the cytosol of said human cells to the nuclei of said cells, whereby vpr would otherwise carry on activities essential to replication of HIV; or a pharmaceutically acceptable salt or ester thereof; together with one or more therapeutic agents useful for treating HIV infected individuals, selected from the group consisting of zidovudine (AZT), acyclovir, ganciclovir, foscarnet, interferon alpha-2a, and interferon alpha-2b; together with a pharmaceutically acceptable carrier therefor.

The present invention still further relates to a method of identifying a compound which is capable of inhibiting or preventing replication of HIV by interfering with the replicatire or other essential functions of vpr by competitively binding to the vpr target in human cells, rip-1, expressed by said HIV, whereby vpr would otherwise carry on activities essential to replication of HIV; said method comprising, in a culture of HIV infected human cells, the step of contacting vpr and rip-2 or a fragment thereof in the presence of said test compound, determining the level of binding and comparing that level to the level of binding that occurs when vpr and rip-1 are contacted in the absence of said test compound. This method also comprises the additional step, where said test compound is determined to have substantially inhibited or prevented formation of said vpr/rip-1 complex by competitively binding to rip-1, of determining the level of p24 produced in said HIV infected cells receiving said test compound, and comparing said level to the level of p24 produced by HIV infected cells having vpr delected from said HIV, as well as to the level of p24 produced in the absence of said test compound.

The present invention also includes a method as described above for identifying a compound which competitively binds to rip-1, wherein said compound also prevents translocation of the vpr/rip-1 complex from the cytosol of said human cells to the nuclei of said cells, or signaling of said translocated complex, whereby vpr would otherwise carry on activities essential to replication of HIV; comprising the additional step of conducting an assay which is capable of determining nuclear colocalization of vpr and rip-1, and determing the level of said colocalization in the presence of said test compound and comparing it to the level of colocalization in the absence of said test compound. Such a may comprise the additional step, where said test compound is determined to have substantially inhibited or prevented said colocalization, of determining the level of p24 produced in said HIV infected cells receiving said test compound, and comparing said level to the level of p24 produced by HIV infected cells having vpr delected from said HIV, as well as to the level of p24 produced in the absence of said test compound.

The present invention still further includes a method of identifying a compound which is a glucocorticoid receptor antagonist and which is capable of inhibiting or preventing replication of HIV by interfering with the replicative or other essential functions of vpr by competitively binding to the vpr target in human cells, rip-1, expressed by said HIV, whereby vpr would otherwise carry on activities essential to replication of HIV; said method comprising the steps of (1) determining glucocorticoid antagonist activity of a test compound, and if said test compound exhibits glucocorticoid antagonist activity, (2) contacting vpr and rip-1 or a fragment thereof in the presence of said test compound, determining the level of binding and comparing that level to the level of binding that occurs when vpr and rip-1 are contacted in the absence of said test compound. This method is particularly one wherein glucocorticoid antagonist activity is measured by determining the effect of said test compound on tyrosine amino-transferase in accordance with the method of Granner and Tompkins, (1970) *Meth. Enzymol.* 15, 633. This method also comprises the additional step, where said test compound is determined to have substantially inhibited or prevented formation of said vpr/rip-1 complex by competitively binding to rip-1, of determining the level of p24 produced in said HIV infected cells receiving said test compound, and comparing said level to the level of p24 produced by HIV infected cells having vpr delected from said HIV, as well as to the level of p24 produced in the absence of said test compound.

The method described above is also one for identifying a glucocorticoid receptor antagonist compound which competitively binds to rip-1, wherein said compound also prevents translocation of the vpr/rip-1 complex from the cytosol of said human cells to the nuclei of said cells, or signaling of said translocated complex, whereby vpr would otherwise carry on activities essential to replication of HIV; and comprises the additional step of conducting an assay which is capable of determining nuclear colocalization of vpr and rip-1, and determing the level of said colocalization in the presence of said test compound and comparing it to the level of colocalization in the absence of said test compound. This method still further comprises the additional step, where said test compound is determined to have substantially inhibited or prevented said colocalization, of determining the level of p24 produced in said HIV infected cells receiving said test compound, and comparing said level to the level of p24 produced by HIV infected cells having vpr delected from said HIV, as well as to the level of p24 produced in the absence of said test compound.

The present invention also relates to a kit for identifying compounds which inhibit vpr protein binding to rip-1 which comprises a first container comprising tyrosine aminotransferase, a second container comprising vpr protein and a third container comprising rip-1 or a fragment thereof; and optionally, in a preferred embodiment of this aspect of the invention, a fourth container comprising an antibody that specifically binds to either the vpr protein or rip-1 is provided.

The present invention involves the use of rip-1, which is essentially pure human protein that has an apparent molecular weight of between 40–43 KD, that occurs in the cytoplasm of human cells, that binds to vpr, and that is transported from the cytoplasm to the nucleus when bound to vpr to form a complex; or a fragment thereof. Rip-1 may be produced by the method comprising the step of culturing a host cell that comprises an expression vector that comprises a nucleotide sequence that encodes rip-1, or a fragment thereof, and isolating the protein or fragment that is produced in the cultured cells.

DETAILED DESCRIPTION OF THE INVENTION

The present invention arises out of the discovery that HIV regulatory protein R, referred to herein as "vpr", binds to a human protein that occurs in the cytoplasm of human cells and that has an apparent molecular weight of between 40–43 KD. It has been discovered that when vpr binds to this human protein, the proteins form a complex which is transported from the cytoplasm to the nucleus. Thus, the human protein acts as a receptor or binding protein for vpr, and is therefore referred to herein as "rip-1".

Action of Glucocorticoid Receptor Antagonists

As used herein, the term "rip-1" is meant to refer to the human protein that has an apparent molecular weight of between 40–43 KD, that occurs in the cytoplasm of human cells, that binds to vpr and that is transported from the cytoplasm to the nucleus when bound to vpr. The rip-1 may be colocalized with the T-cell and B-cell transcription factor NFκB. It has been discovered that the rip-1 behaves as a member of the steroid hormone receptor superfamily, and particularly, that it behaves as a member of the glucocorticoid receptor (GR) family, and more particularly, that it behaves as a GR type II receptor molecule.

The discovery that the rip-1 in human cells behaves as a member of the steroid hormone receptor superfamily, especially the glucocorticoid receptor family, elucidates the manner in which the binding of vpr to rip-1 is involved in HIV replication and thus pathogenesis. Accordingly, preventing or inhibiting such interaction by blocking the rip-1 with a different compound that competitively binds to it, effectively inactivates vpr and prevents it from converting cells to better HIV replication hosts. The identification of compounds which can inhibit the effects of vpr and thereby inhibit HIV replication in HIV infected cells is based on the discovery that many of the actions of vpr are analogous to those of a glucocorticoid. The mechanism of action of vpr allows for the targeting of that mechanism for active intervention, and thereby the rational design and selection of anti-HIV compounds.

The cellular trafficking characteristics which have been observed for rip-1 are consistent with rip-1 being a member of the steroid hormone receptor superfamily. The glucocorticoid and mineralocorticoid receptors are the only members of this protein family which translocate from the cytoplasm to the nucleus upon exposure to their ligand. Two types of glucocorticoid receptors have been described. Type I receptors are concentrated in the nucleus even when there is no ligand present. Type II receptors specifically concentrate in the cytoplasm in the absence of ligand, and only translocate to the nucleus in the presence of their appropriate stimulating hormone. The two types of gtucocorticoid receptors have high affinity for their specific ligands, and are considered to function through the same transduction pathways. The main functional difference between these two classes of receptors is that the type II receptors are activated by their ligands in such a way that they only transactivate their target cellular protooncogenes in some, but not in all cells. Such cellular specificity is not observed in type I receptors. These observations are consistent with rip-1 being type II molecule.

Glucocorticoid receptors have a number of roles. Glucocorticoid receptors have been shown to act as a powerful transactivator. Glucocorticoid receptors have also been shown to operate through the repression of gene expression for particular open reading frames. Glucocorticoid receptor mediated repression is attained by competition for the sites on the DNA molecule which would otherwise be bound by transactivators. An example of the latter is the specific bilateral relationship which has been described for glucocorticoid receptors and c-Jun. In this case, the glucocorticoid receptor represses c-Jun activity, and the opposite is also observed. The phorbol ester PMA has been reported to activate transcription of the AP-1/c-Jun promoter. In addition, glucocorticoids have been shown to counter lymphokine activity as observed by the inhibition of proliferation of a variety of cell lines. This mechanism is deemed to affect immunoregulatory mechanisms in areas such as T cell activation, which is in part mediated by the Jun/AP-1 activity, and its resulting lymphokines. The observation of a cessation in proliferation in different cell lines transfected with vpr is considered explained by a glucocorticoid receptor mediated pathway, in which rip-1 acts to bridge viral and cellular activities.

It is also important to note that the glucocorticoid receptors function as a part of a larger multimeric complex. These 330 KD protein clusters comprise a heat shock protein 90 dimer, a heat shock protein 56 unit, and sometimes by a heat shock protein 70 unit (HSP 70), in addition to the specific glucocorticoid receptor molecule; and rip-1 has been observed in association with this HSP 70. The glucocorticoid receptor polypeptide itself is usually composed of three functional domains arranged in a linear configuration; a hormone binding domain, a DNA binding domain, and a third domain which has been shown to interact with additional cellular proteins, defining the trafficking characteristics of this gene product. Rip-1 is the first vpr associating protein which has been identified in accordance with the present invention, but it is possible that other gene products may either interact with vpr directly, or indirectly through rip-1 mediated associations. The relationship between vpr and the glucocorticoid receptor related heat shock proteins which is deemed to exist in accordance with the present invention, dictates that rip-1 be considered a member of the steroid hormone receptor superfamily. In addition, this will indicate what cellular functions respond to vpr caused cellular disregulation effects which vpr has been observed to induce.

In accordance with the principles set out above, the present invention provides for treatment of individuals infected with HIV by administering to them a therapeutically effective amount of a compound which is asteroid hormone receptor antagonist that competitively binds to rip-1, preventing or inhibiting formation and translocation of the vpr/rip-1 complex. Particularly, the present invention provides for such treatment by administration of a therapeutically effective amount of a glucocorticoid receptor antagonist, especially a type II glucocorticoid receptor antagonist.

As used herein, the term "glucocorticoid receptor antagonist" simply means any compound which will bind to the glucocorticoid receptor, and which will, therefore, also competitively bind to rip-1 so as inhibit or prevent formation of the vpr/rip-1 complex. In this context, the term "antagonist" refers to the blocking of the rip-1 receptor by the compound, thus preventing the natural ligand, vpr, from binding to it, thus creating an antagonism by preventing the agonist from acting. With respect to the glucocorticoid receptor itself, however, it is not necessary that the compound be, strictly speaking, a glucocorticoid antagonist, i.e., have antiglucocorticoid activity. Thus, such a compound may be either an agonist or antagonist; however, it is preferred to select compounds which have antiglucocorticoid activity, i.e., which bind to the glucocorticoid receptor but do not have glucocorticoid agonist activity. Such compounds will competitively bind to rip-1, but will not, in the cases where such compounds also bind to glucocorticoid receptors in the cells of the individual ungoing treatment for the HIV infection, produce the effects and activities of glucocorticoids, which may be undesirable over extended periods of time. For such agonists, the overall result will be dependent upon the initial dosage as well as the amount of compound which is bound to rip-1, not to mention the extent of binding to glucocorticoid receptors and resultant agonist activity in the individual involved. Thus, it is still within the scope of the present invention to use glucocorticoid agonists, although this is not preferred, and the choice of the type, i.e., glucocorticoid receptor agohist or antagonist, as well as of the specific compound, can be made in a straight-forward manner using evaluation procedures well known in the art and described herein.

It is possible to identify compounds which have antiglucocorticoid activity by determining the effect of a candidate compound on the tyrosine amino-transferase enzyme. The test system is based on measurement of the activity of the liver enzyme tyrosine amino-transferase (TAT) in cultures of rat hepatoma cells (RHC). The enzyme catalyzes the first step in the metabolism of tyrosine and can be induced by glucorcorticoids both in the liver and in hepatoma cells. The activity is readily measured in raw extracts. TAT converts the amino group of tyrosine to 2-oxoglutaric acid, and p-hydroxyphenylpyruvate is also formed, which is converted to the more stable p-hydroxybenzaldehyde in alkaline solution. Its measured adsorption line lies at 331 nm. More details concerning this procedure may be found in Granner and Tomkins (1970) *Meth. Enzymol.* 15, 633.

In accordance with the present invention, a preferred group of glucocorticoid receptor antagonists are those to which mifepristone, better known as RU-486, belongs. This compound, 11β-(4-dimethylaminophenyl)-17β-hydroxy-17α-(propyl-1-ynyl)estra-4,9-dien-3-one, is a good glucocorticoid antagonist, which also has antiprogestin activity. Further details concerning this and related compounds may be found in Agarwal, M. K. et al. "Glucocorticoid antagonists" *FEBS LETTERS* 217, 221–226 (1987). Extensive work has been done over the years in synthesizing and testing glucocorticoid antagonists which belong to this group, and the published literature is an abundant guide for the selection of candidate compounds that fall within the scope of the present invention. The patent literature alone is substantial. Thus, reference is made to the following U.S. patents, all of which are incorporated herein by reference in their entirety: 4,296,206; 4,386,085; 4,447,424; 4,477,445; 4,519,946; 4,540,686; 4,547,493; 4,634,695; 4,634,696; 4,753,932; 4,774,236; 4,814,327; 4,829,060; 4,861,763; 4,912,097; 4,943,566; 4,954,490; 4,978,657; 5,006,518; 5,043,332; 5,064,822; 5,073,548; 5,089,488; 5,089,635; 5,093,507; 5,095,010; 5,095,129; 5,132,299; 5,166,146; and 5,276,023. Analysis of the patents set out above and the attendant technical literature reveals that the 11-position substituent, and particularly the size of that substituent, plays a key role in determining the antiglucocorticoid activity, although the character of the A ring is also important. It is also noted that a 17-hydroxypropenyl side chain generally decreases antiglucocorticoidal activity in comparison to the 17-propinyl side chain containing compounds, and that generally 9α, 10α-$CH_2$ groups decrease antiglucocorticoidal activity.

Action of vpr

The human immunodeficiency virus has been termed a complex retrovirus due to the fact that the HIV genome encodes six regulatory genes (tat, rev, vif, vpr, vpu, nef) in addition to the common gag, pol and env open reading frames found in all retroviruses. The complexity of HIV and its related lentiviruses can furthermore be attributed to the intricate patterns of regulation of gene expression observed during the vital lifecycle. All such regulatory mechanisms are accomplished by the interaction of virally encoded proteins with distinct host cell factors.

Many cellular proteins are needed for HIV gene expression during the infection process, e.g., the HIV tat gene has been shown to be a nondispensable regulatory gene responsible for the transactivation of the viral LTR. The vpr gene of HIV-1 encodes a 15 KD polypeptide. Vpr has a highly conserved nucleotide sequence among the different primate lentiviruses. All HIV-1 and HIV-2, as well as all pathogenic SIV isolates have a vpr gene. Vpr has several activities which are involved in HIV infection. See PCT application Ser. No. PCT/US 94/02191 (Docket No. 63); U.S. application Ser. No. 08/019,601 (Docket No. 3); and U.S. application Ser. No. 08/167,608 (Docket No. 8), each of which are incorporated herein by reference in their entirety. In particular, vpr is deemed to enhance retroviral infection by causing changes in cells that make them better hosts for HIV replication, all of which has been explained in detail further above in the section which describes the prior art.

Action of rip-1

The method of treating individuals infected with HIV in accordance with the present invention is based on the administration of compounds which prevent or inhibit the formation of the vpr/rip-1 complex and its translocation from the cytoplasm, i.e., cytosol, to the nucleus. Thus, an important aspect of the present invention is a procedure for obtaining essentially pure human rip-1. As already noted, rip-1 has an apparent molecular weight of between 40–43 KD and occurs in the cytoplasm of human cells, and unbound, is a cytosolic protein. When bound to vpr, the rip-1 protein forms a complex with vpr and the complex translocates from the cytoplasm to the nucleus. The rip-1 can be isolated from human cells by passing a human cell preparation through an immobilized vpr column under conditions which allow vpr/rip-1 binding, and then changing the conditions to those which do not favor such binding. The released rip-1 can be collected in essentially pure form. Further purification may be achieved using routine chromatography means.

The following procedure may be used to purify rip-1s. Cell extracts from primary T cells and monocytes as well as peripheral blood cells and macrophages are obtained by methods known to those skilled in the art. Cell extracts are separated by affinity chromatography. Briefly, eukaryotically-produced vpr is immobilized to a solid support matrix via one or more covalent bonds. Solid support matrices include agarose, polyacrylamide-agarose, controlled-pore glass and other such materials known to those skilled in the art. One skilled in the art will readily appreciate the standard techniques involved in coupling vpr to the matrix as well as techniques involved in activation of the matrix. A spacer molecule may be employed to distance vpr from the matrix backbone in order to allow vpr to more freely bind proteins in the cell extract. One skilled in the art will readily appreciate the variety of spacer molecules with which to use.

The cell extract is layered onto the vpr affinity column by standard methods known to those skilled in the art. Appropriate buffers, washing conditions and elution conditions, which are known to those skilled in the art, are chosen. The resulting eluate may be further purified to homogeneity by techniques such high performance liquid chromatography (HPLC) or other such methods as known to those skilled in the art.

The rip-1 has been purified to approximately 95% purity by a vpr-affinity column using this technique of purification. Said protein has a molecular weight of about 40–43 KD when separated by reducing SDS-PAGE. The protein has been detected in rhabdomyosarcoma cell lines TE 671 and RD; osteosarcoma cell lines D17 and HOS; glioblastoma cell lines HTB14, U373 and HBT10; as well as T-cell lines Supt-1 and H9 and monocyte/macrophage lines U937, THP-1, KG-1 and HL-60 as well as primary cells. Further details may be found in Examples 6 further below.

Techniques for the cloning of a protein are widely known to those skilled in the art. Briefly, a pure preparation of the 41 KD cellular protein that binds vpr (the rip-1) is sequenced by standard N-terminal sequencing techniques known to those skilled in the art. A set of oligonucleotide probes coding for the deduced amino acid sequence of the N-terminal portion of the rip-1 is designed by techniques known to those skilled in the art. This set of probes is used to screen a human cDNA library by techniques known to those skilled in the art. Positive plaques are selected and sequenced by methods such as dideoxy sequencing for the entire nucleotide sequence of the rip-1.

Alternatively, a pure preparation of the rip-1 may be injected into a mammal, such as a rabbit or mouse, resulting in the production of a polyclonal antiserum. Such immunization procedures are well known to those skilled in the art. In addition, plasma cells (antibody-producing B cells) may be isolated from the injected mammal and fused with myeloma cells to produce hybridomas which produce monoclonal antibodies. Additionally, recombinant antibodies can be produced by a variety of methods; and such methods are well known to those skilled in the art. The polyclonal antiserum may be used to screen a human cDNA expression library wherein cells expressing the rip-1 may be identified with the antiserum. Positive clones are selected and the DNA isolated and sequenced by methods known to those skilled in the art.

Once the complete nucleotide sequence of the rip-1 is known, the sequence, or any portion thereof, can be incorporated into a plasmid vector or any other vector capable of expressing the rip-1. In addition, mammalian cells as well as bacterial cells may be transformed with the plasmid construct containing the sequence, or derivatives thereof, encoding the rip-1. Said transformed cells may produce the rip-1 intracellularly or extracellularly. In addition, oligonucleotides corresponding to the portions of the sense or antisense of the rip-1 may also be produced. These oligonucleotides may comprises between 10 and 5000 nucleotides, preferably between 10 and 500 nucleotides, most preferably between 10 and 100 nucleotides.

The present invention thus involves a nucleic acid molecule that comprises a nucleotide sequence that encodes rip-1 or a fragment thereof; an expression vector that comprises such a nucleotide sequence; a host cell which comprises such an expression vector; a method of producing rip-1 or a fragment thereof comprising the step of culturing such a host cell.

Rip-1 may be produced by routine means using readily available starting materials as described above. Provision of a suitable DNA sequence encoding the desired protein permits the production of the protein using recombinant techniques now known in the art. The DNA sequence may also be obtained from other sources of HIV DNA or can be prepared chemically using a synthesized nucleotide sequence. When the coding DNA is prepared synthetically, advantage can be taken of known codon preferences of the intended host where the DNA is to be expressed.

One having ordinary skill in the art can, using well known techniques, obtain a DNA molecule encoding the rip-1 and insert that DNA molecule into a commercially available expression vector for use in well known expression systems. For example, the commercially available plasmid pSE420 (Invitrogen, San Diego, Calif.) may be used for production in E. coli. The commercially available plasmid pYES2 (Invitrogen, San Diego, Calif.) may be used for production in S. cerevisiae strains of yeast. The commercially available MaxBac™ (Invitrogen, San Diego, Calif.) complete baculovirus expression system may be used for production in insect cells. The commercially available plasmid pcDNA I (Invitrogen, San Diego, Calif.) may be used for production in may be used for production in mammalian cells such as Chinese Hamster Ovary cells. One having ordinary skill in the art can use these commercial expression vectors systems or others to produce rip-1 using routine techniques and readily available starting materials.

One having ordinary skill in the art may use other commercially available expression vectors and systems or produce vectors using well known methods and readily available starting materials. Expression systems containing the requisite control sequences, such as promoters and polyadenylation signals, and preferably enhancers, are readily available and known in the art for a variety of hosts. See e.g., Sambrook et al., *Molecular Cloning a Laboratory Manual*, Second Ed. Cold Spring Harbor Press (1989). Thus, the desired proteins can be prepared in both prokaryotic and eukaryotic systems, resulting in a spectrum of processed forms of the protein.

The most commonly used prokaryotic system remains *E. coli*, although other systems such as *B. subtilis* and Pseudomonas are also useful. Suitable control sequences for prokaryotic systems include both constitutive and inducible promoters including the lac promoter, the trp promoter, hybrid promoters such as tac promoter, the lambda phage Pl promoter. In general, foreign proteins may be produced in these hosts either as fusion or mature proteins. When the desired sequences are produced as mature proteins, the sequence produced may be preceded by a methionine which is not necessarily efficiently removed. Accordingly, the peptides and proteins claimed herein may be preceded by an N-terminal Met when produced in bacteria. Moreover, constructs may be made wherein the coding sequence for the peptide is preceded by an operable signal peptide which results in the secretion of the protein. When produced in prokaryotic hosts in this manner, the signal sequence is removed upon secretion.

A wide variety of eukaryotic hosts are also now available for production of recombinant foreign proteins. As in bacteria, eukaryotic hosts may be transformed with expression systems which produce the desired protein directly, but more commonly signal sequences are provided to effect the secretion of the protein. Eukaryotic systems have the additional advantage that they are able to process introns which may occur in the genomic sequences encoding proteins of higher organisms. Eukaryotic systems also provide a variety of processing mechanisms which result in, for example, glycosylation, carboxy-terminal amidation, oxidation or derivatization of certain amino acid residues, conformational control, and so forth.

Commonly used eukaryotic systems include, but is not limited to, yeast, fungal cells, insect cells, mammalian cells, avian cells, and cells of higher plants. Suitable promoters are available which are compatible and operable for use in each of these host types as well as are termination sequences and enhancers, as e.g. the baculovirus polyhedron promoter. As above, promoters can be either constitutive or inducible. For example, in mammalian systems, the mouse metallothionene promoter can be induced by the addition of heavy metal ions.

The particulars for the construction of expression systems suitable for desired hosts are known to those in the art. For recombinant production of the protein, the DNA encoding it is suitably ligated into the expression vector of choice and then used to transform the compatible host which is then cultured and maintained under conditions wherein expression of the foreign gene takes place. The protein of the present invention thus produced is recovered from the culture, either by lysing the cells or from the culture medium as appropriate and known to those in the art.

One having ordinary skill in the art can, using well known techniques, isolate the rip-1 or fragments thereof produced using such expression systems.

In addition to isolating rip-1 from natural sources and producing rip-1 or fragments thereof by recombinant techniques, automated amino acid synthesizers may also be employed to produce rip-1 or fragments thereof. It should be further noted that if the proteins herein are made synthetically, substitution by amino acids which are not encoded by the gene may also be made. Alternative residues include, for example, the ω amino acids of the formula $H_2N(CH_2)_nCOOH$ wherein n is 2–6. These are neutral, nonpolar amino acids, as are sarcosine (Sar), t-butylalanine (t-BuAla), t-butylglycine (t-BuGly), N-methyl isoleucine (N-MeIle), and norleucine (Nleu). Phenylglycine, for example, can be substituted for Trp, Tyr or Phe, an aromatic neutral amino acid; citrulline (Cit) and methionine sulfoxide (MSO) are polar but neutral, cyclohexyl alanine (Cha) is neutral and nonpolar, cysteic acid (Cya) is acidic, and ornithine (Orn) is basic. The conformation conferring properties of the proline residues may be obtained if one or more of these is substituted by hydroxyproline (Hyp).

Pharmaceutical Compositions and Methods of Treatment

The pharmaceutical compositions of the present invention comprise a therapeutically effective amount of a composition comprising one or more steroid hormone receptor antagonists, preferably glucocorticoid receptor antagonists, and more preferably glucocorticoid receptor Type II antagonists, which by binding to rip-1 or a fragment thereof, a glucocorticoid type molecule, prevents vpr from binding to rip-1, and thereby prevents translocation of the vpr/rip-1 complex from the cytosol to the nucleus of the infected cell, where vpr carries on its various activities essential to replication of HIV.

The pharmaceutical composition comprising the receptor antagonist which binds rip-1 or a fragment thereof and a pharmaceutically acceptable carrier or diluent may be formulated by one having ordinary skill in the art with compositions selected depending upon the chosen mode of administration. Suitable pharmaceutical carriers are described in the most recent edition of *Remington's Pharmaceutical Sciences,* A. Osol, a standard reference text in this field.

For parenteral administration, the receptor antagonist which binds rip-1 or a fragment thereof can be, for example, formulated as a solution, suspension, emulsion or lyophilized powder in association with a pharmaceutically acceptable parenteral vehicle. Examples of such vehicles are water, saline, Ringer's solution, dextrose solution, and 5% human serum albumin. Liposomes and nonaqueous vehicles such as fixed oils may also be used. The vehicle or lyophilized powder may contain additives that maintain isotonicity (e.g., sodium chloride, mannitol) and chemical stability (e.g., buffers and preservatives). The formulation is sterilized by commonly used techniques. For example, a parenteral composition suitable for administration by injection is prepared by dissolving 1.5% by weight of active ingredient in 0.9% sodium chloride solution.

The pharmaceutical compositions according to the present invention may be administered as a single doses or in multiple doses. The pharmaceutical compositions of the present invention may be administered either as individual therapeutic agents or in combination with other therapeutic agents. The treatments of the present invention may be combined with conventional therapies, which may be administered sequentially or simultaneously. In particular, the pharmaceutical compositions may comprise a therapeutically effective amount of one or more of said receptor antagonists, together with one or more therapeutic agents useful for treating HIV infected individuals, selected from the group consisting of zidovudine (AZT), acyclovir, ganciclovir, foscarnet, interferon alpha-2a, and interferon alpha-2b, together with a pharmaceutically acceptable carrier.

The pharmaceutical compositions described above may be administered by any means that enables the active agent to reach the agent's site of action in the body of a mammal. The dosage administered varies depending upon factors such as: pharmacodynamic characteristics; its mode and route of administration; age, health, and weight of the recipient; nature and extent of symptoms; kind of concurrent treatment; and frequency of treatment. Usually, a daily dosage of the receptor antagonist that binds rip-1 can be about 1 μg to 100 milligrams per kilogram of body weight. Ordinarily 0.01 to 50, and preferably 0.1 to 20 milligrams per kilogram per day given in divided doses 1 to 6 times a day or in sustained release form is effective to obtain desired results.

The present invention relates to a method for treating HIV infected individuals or individuals exposed to HIV, comprising administering to such individuals a therapeutically effective amount of a composition comprising one or more steroid hormone receptor antagonists, preferably glucocorticoid receptor antagonists, more preferably glucocorticoid receptor Type II receptor antagonists, which bind rip-1 and prevent vpr from binding to rip-1, and thereby prevent translocation of the vpr/rip-1 complex from the cytosol to the nucleus of the infected cell, where vpr carries on its various activities essential to replication of HIV.

The present invention also relates to such a method of treating HIV infected individuals as described above, wherein there is coadministered with one or more of said receptor antagonists, one or more therapeutic agents useful for treating HIV infected individuals, selected from the group consisting of zidovudine (AZT), acyclovir, ganciclovir, foscarnet, interferon alpha-2a, and interferon alpha-2b.

Identifyiny Compounds which Bind rip-1

The present invention also relates to a method of identifying such compounds which inhibit or prevent replication of HIV by interfering with the replicative or other essential functions of vpr by competitively binding to the vpr target in human cells, rip-1, said compounds comprising glucocorticoid receptor (GR) antagonists, which by binding to rip-1, a GR type molecule, prevents vpr from binding to rip-1. This method of identifying compounds which inhibit vpr binding to rip-1 comprises the steps of (1) determining glucocorticoid antagonist activity of a test compound by determining the effect of said test compound on tyrosine amino-transferase in accordance with the method of Granner and Tompkins, (1970) *Meth. Enzymol.* 15, 633; and if said test compound exhibits glucocorticoid antagonist activity, (2) contacting vpr and rip-1 or a fragment thereof in the presence of said test compound, determining the level of binding and comparing that level to the level of binding that occurs when vpr and rip-1 are contacted in the absence of said test compound. Compounds which are thus identified, interfere with the binding of vpr to rip-1, and are thus useful to impede HIV replication; therefore such compounds will be useful as anti-HIV therapeutics alone or as part of a multi-faceted anti-HIV drug regimen which includes other therapeutics.

To practice these aspects of the invention, once a test compound has been found to be a glucocorticoid receptor antagonist, vpr protein and rip-1 are contacted in the presence of said test compound. The level of binding of the proteins is determined. The resultant level of binding is compared to the known level of binding that occurs when both proteins are contacted with each other in the absence of a test compound. In the absence of a compound that interferes with the binding, the two proteins will bind. As a control, vpr protein and rip-1 are contacted in the absence of a test compound.

Test compound is provided, preferably in solution. Serial dilutions of test compounds may be used in a series of assays. Test compound may be added at concentrations from 0.01 μM to 1M. A preferred range of final concentrations of a test compound is from 10 μM to 100 μM.

Production of vpr protein is described in the U.S. patent applications cited above which have been incorporated by reference. A preferred concentration range of the vpr used is about 1 μg/ml to 1 mg/ml. A preferred concentration of the vpr is about 50 μg/ml.

The rip-1 may be produced by routine means using readily available starting materials following the teachings described herein. A preferred concentration range of the rip-1 used is about 1 μg/ml to 1 mg/ml. A preferred concentration of the rip-1 is about 50 μg/ml.

The means to detect whether or not vpr and rip-1 are bound, or if binding has been inhibited, are routine and include enzyme assays and ELISA assays. One having ordinary skill in the art can detect protein binding using well known methods. One having ordinary skill in the art can readily appreciate the multitude of ways to practice a binding assay to detect compounds which modulate the binding of vpr to rip-1. For example, antibodies are useful for immunoassays which detect or quantirate vpr protein binding to rip-1. The immunoassay typically comprises incubating vpr protein and rip-1 to allow protein-protein binding in the presence of a detectably labeled high affinity antibody capable of selectively binding to either vpr protein or rip-1, and detecting the labeled antibody which is bound to the protein. Various immunoassay procedures are described in *Immunoassays for the 80's*, A. Voller et al., Eds., University Park, 1981.

In this aspect of the invention, the antibody or either vpr protein or rip-1 may be added to nitrocellulose, or other solid support which is capable of immobilizing proteins. The support may then be washed with suitable buffers followed by treatment with the detectably labeled vpr-specific antibody or the antibody that binds to the rip-1. The solid phase support may then be washed with the buffer a second time to remove unbound antibody. The amount of bound label on said solid support may then be detected by conventional means.

By "solid phase support" or "carrier" is intended any support capable of binding antigen or antibodies. Well-known supports or carriers, include glass, polystyrene, polypropylene, polyethylene, dextran, nylon, amylases, natural and modified celluloses, polyacrylamides, agaroses, and magnetite. The nature of the carrier can be either soluble to some extent or insoluble for the purposes of the present invention. The support configuration may be spherical, as in a bead, or cylindrical, as in the inside surface of a test tube, or the external surface of a rod. Alternatively, the surface may be flat such as a sheet, test strip, etc. Those skilled in the art will know many other suitable carriers for binding antibody or antigen, or will be able to ascertain the same by use of routine experimentation.

The binding activity of a given lot of antibodies may be determined according to well known methods. Those skilled in the art will be able to determine operative and optimal assay conditions for each determination by employing routine experimentation.

Positive control assays may be performed in which no test compound is added.

One of the ways in which the antibodies can be detectably labeled is by linking the same to an enzyme and use in an enzyme immunoassay (EIA), or enzyme-linked immunosorbent assay (ELISA). This enzyme, when subsequently exposed to its substrate, will react with the substrate generating a chemical moiety which can be detected, for example, by spectrophotometric, fluorometric or by visual means. Enzymes which can be used to detectably label the antibody include, but are not limited to, malate dehydrogenase, staphylococcal nuclease, delta-5-steroid isomerase, yeast alcohol dehydrogenase, alpha-glycerophosphate dehydrogenase, triose phosphate isomerase, horseradish peroxidase, alkaline phosphatase, asparaginase, glucose oxidase, beta-galactosidase, ribonuclease, urease, catalase, glucose-6phosphate dehydrogenase, glucoamylase and acetylcholinesterase.

By radioactively labeling the antibody, it is possible to detect it through the use of a radioimmunoassay (RIA) (see, for example, Work, T. S., et al., *Laboratory Techniques and Biochemistry in Molecular Biology*, North Holland Publishing Company, N.Y., 1978. The radioactive isotope can be detected by such means as the use of a gamma counter or a scintillation counter or by autoradiography. Isotopes which are particularly useful for the purpose of the present invention are: $^{3}H$, $^{125}I$, $^{131}I$, $^{35}S$, $^{14}C$, and, preferably, $^{125}I$.

It is also possible to label the antibody with a fluorescent compound. When the fluorescent labeled antibody is exposed to light of the proper wave length, its presence can then be detected due to fluorescence. Among the most commonly used fluorescent labelling compounds are fluorescein isothiocyanate, rhodamine, phycoerythrin, phycocyanin, allophycocyanin, o-phthaldehyde and fluorescamine.

The antibody can also be detectably labeled using fluorescence-emitting metals such as $^{152}Eu$, or others of the lanthanide series. These metals can be attached to the TNF-specific antibody using such metal chelating groups as diethylenetriaminepentaacetic acid (DTPA) or ethylenediaminetetraacetic acid (EDTA).

The antibody also can be detectably labeled by coupling to a chemiluminescent compound. The presence of the chemiluminescently labeled antibody is then determined by detecting the presence of luminescence that arises during the course of a chemical reaction. Examples of particularly useful chemiluminescent labeling compounds are luminol, isoluminol, theromatic acridinium ester, imidazole, acridinium salt and oxalate ester.

Likewise, a bioluminescent compound may be used to label the antibody. Bioluminescence is a type of chemiluminescence found in biological systems in which a catalytic protein increases the efficiency of the chemiluminescent reaction. The presence of a bioluminescent protein is determined by detecting the presence of luminescence. Important bioluminescent compounds for purposes of labeling are luciferin, luciferase and aequorin. Detection of the vpr-specific antibody or the antibody that binds to the rip-1 may be accomplished by a scintillation counter, for example, if the detectable label is a radioactive gamma emitter, or by a fluorometer, for example, if the label is a fluorescent material.

In the case of an enzyme label, the detection can be accomplished by colorometric methods which employ a substrate for the enzyme. Detection may also be accomplished by visual comparison of the extent of enzymatic reaction of a substrate in comparison with similarly prepared standards.

As can be readily appreciated, one of the viral proteins may also be detectable and serve as a reporter molecule instead of or in addition to the antibody.

The components of the assay may be adapted for utilization in an immunometric assay, also known as a "two-site" or "sandwich" assay. In a typical immunometric assay, a quantity of unlabeled antibody (or fragment of antibody) is bound to a solid support that is insoluble in the fluid being tested and a quantity of detectably labeled soluble antibody is added to permit detection and/or quantitation of the ternary complex formed between solid-phase antibody, antigen, and labeled antibody.

Typical and preferred immunometric assays include "forward" assays in which the antibody bound to the solid phase is first contacted with the one of the viral proteins to immobilize it. The second vital protein is added in the presence of the test compound. After a suitable incubation period, the solid support is washed to remove unbound protein. A second antibody is then added which is specific for the second vital protein. The second antibody is preferably detectable. After a second incubation period to permit the labeled antibody to complex with the second viral protein bound to the solid support through the unlabeled antibody and first viral protein, the solid support is washed a second time to remove the unreacted labeled antibody. This type of forward sandwich assay may be a simple "yes/no" assay to determine whether binding has occurred or may be made quantitative by comparing the measure of labeled antibody with that obtained in a control. Such "two-site" or "sandwich" assays are described by Wide, Radioimmune Assay Method, Kirkham, Ed., E. & S. Livingstone, Edinburgh, 1970, pp. 199–206).

Other type of "sandwich" assays are the so-called "simultaneous" and "reverse" assays. A simultaneous assay involves a single incubation step wherein the antibody bound to the solid support and labeled antibody, both viral protein and the test compound are added at the same time.

After the incubation is completed, the solid support is washed to remove uncomplexed proteins. The presence of labeled antibody associated with the solid support is then determined as it would be in a conventional "forward" sandwich assay.

In the "reverse" assay, stepwise addition first of a solution of labeled antibody to the viral proteins followed by the addition of unlabeled antibody bound to a solid support after a suitable incubation period, is utilized. After a second incubation, the solid phase is washed in conventional fashion to free it of the residue of the sample being tested and the solution of unreacted labeled antibody. The determination of labeled antibody associated with a solid support is then determined as in the "simultaneous" and "forward" assays. In one embodiment, a combination of antibodies of the present invention specific for separate epitopes may be used to construct a sensitive three-site immunoradiometric assay.

In some preferred embodiments, an anti-vpr antibody is fixed to a solid phase. Vpr protein is contacted with the fixed antibody to form a complex. The complex is contacted with a rip-1 in the presence of a test compound. Antibodies that bind to the rip-1 are then added. The solid phase is washed to removed unbound material. A control assay is performed in an identical manner except that no test compound is used. Detection of the antibodies that bind to the rip-1 indicates that the vpr and rip-1s are capable of binding to each other in the presence of the test compound. Accordingly, failure to detect that antibodies that bind to vpr protein indicates that the test compound inhibits binding of vpr and rip-1s. Quantifying the level of binding in the presence and absence of test compound allows for the measurement of the extent of modulation that the test compound can cause on vpr binding to rip-1.

In some preferred embodiments, antibodies that bind to the rip-1 are fixed to a solid phase. Rip-1 is contacted with the fixed antibody to form a complex. The complex is contacted with vpr protein in the presence of a test compound. Anti-vpr antibodies are then added. The solid phase is washed to removed unbound material. A control assay is performed in an identical manner except that no test compound is used. Detection of the antibodies that bind to vpr protein indicates that the vpr and rip-1s are capable of binding to each other in the presence of the test compound. Accordingly, failure to detect that antibodies that bind to vpr protein indicates that the test compound inhibits binding of vpr and rip-1s. Quantifying the level of binding in the presence and absence of test compound allows for the measurement of the extent of modulation that the test compound can cause on vpr binding to rip-1.

In the methods of identifying compounds that inhibit vpr protein binding to rip-1, fragments of vpr may be used provided the fragment used retains its ability to bind to the rip-1. Similarly, fragments of rip-1 may be used provided the fragment used retains its ability to bind to vpr protein.

A further aspect of the present invention relates to kits for practicing the above described method of identifying compounds which are glucocorticoid receptor antagonists and which inhibit vpr protein binding to rip-1. Kits according to this aspect of the invention comprises a first container comprising tyrosine amino-transferase, a second container comprising vpr protein, and a third container comprising rip-1. Additionally, to practice the above defined method, means are required to distinguish vpr protein bound to the rip-1 from unbound vpr protein or unbound rip-1. In a preferred embodiment of this aspect of the invention, a fourth container comprising an antibody that specifically binds to either the vpr protein or rip-1 is provided. At least one of the contained components, preferably the antibody, may be conjugated with an agent, such as those described above, which allows its presence to be detected. In another preferred embodiment of this aspect of the invention, a fourth container is provided which contains an antibody that specifically binds to either the vpr protein or rip-1, but not the protein which is bound by the antibody in the third container. At least one of the contained components, preferably the antibody, may be conjugated with an agent, such as those described above, which allows its presence to be detected. In the kits of the invention which are useful to practice the methods of identifying compounds that inhibit vpr protein binding to a protein, fragments of vpr may be included provided the fragment used retains its ability to bind to the rip-1. Similarly, fragments of rip-1 may be included, provided the fragment used retains its ability to bind to vpr protein.

The present invention involves the use of antibodies that specifically bind to rip-1. Production of such antibodies can be achieved by those having ordinary skill in the art without undue experimentation using readily available starting materials. The antibodies are useful in the assay to identify compounds that inhibit vpr binding to rip-1, described above.

Another aspect of the invention relates to methods of identifying compounds which bind to rip-1, but which do not translocate to the nucleus as a complex with said receptor. By binding to rip-1 but not translocating, the compounds inhibit vpr activity by competing with vpr for rip-1 receptor binding, while not being active once bound. As used herein, such compounds which bind to the rip-1 to form a complex that does not translocate, are deemed vpr receptor antagonists. Compounds which form complexes with the rip-1 that do not translocate into the nucleus are useful to impede HIV replication; therefore such compounds will be useful as anti-HIV therapeutics alone or as part of a multi-faceted anti-HIV drug regimen which includes other therapeutics.

EXAMPLES OF PREFERRED EMBODIMENTS

EXAMPLE 1

Expression and Purification of Recombinant HIV-1 vpr

The expression and purification of HIV-1 vpr expressed in insect cells was carried out. The vpr open reading frame from HIV-1 NL 43 was cloned into the baculovirus expression vector pVL1393. This construct was subsequently cotransfected into *Spodoptera fungupeida* (sf-9) cells with linearized DNA from Autograph California nuclear polyhidrosis virus (Baculogold-AcMNPV). The recombinant baculoviruses obtained were subsequently plaque purified and expanded following published protocols.

Recombinant vpr was produced by the following procedures. High five cells were infected at 5–10 MOI, and a cell density of 2×10(6) cells/ml. The tissue culture supernatants were harvested 24 hours later. These were centrifuged at 10000 g and supplemented with a protease inhibitor cocktail (PMSF, EDTA, EGTA, aprotinin, pepstatin A, and Leupetin. All supernatants were kept on ice until use.

The above-described supernatants were passed over a rabbit anti vpr affinity column constructed following published procedures. The elution scheme consisted of preelution with 100 mM Phosphate buffer, pH 8.0, followed by the elution buffer: 100 mM triethanolamine, pH 11.5. The eluate was collected in 0.5 ml aliquots and neutralized with 1/20 of the total fraction volume of 1M sodium phosphate, pH 6.8. These fractions were monitored for protein concentration, and were further analyzed by ELISA, silver stain, and western blot.

EXAMPLE 2

Vpr Antibodies

The rabbit anti-vpr peptide 2–21 (808) was obtained from NIH, AIDS RR. All the other antibodies used were made as described in published procedures. These antibodies are LR1, a rabbit anti-vpr. This serum was obtained by immunizing an animal with the purified, recombinant vpr described further above. A mouse anti-vpr was also used, raised against the same antigen. Mouse antisera to vpr peptide 2–21, is denoted as m. anti p1; mouse antisera to vpr peptide 90–96 is denoted as m. anti p3. Another mouse antisera was obtained to vpr peptide 41–48; this is denoted as m. anti p2. All of these sera were titered by ELISA, and tested for their crossreactivities with peptides and recombinant vpr prior to use.

EXAMPLE 3

Enzyme Linked Immunosorbent Assays (ELISAs)

Three different variations of the ELISA technique were used. A solid phase approach was the one used, unless otherwise noted. A capture ELISA system, and a protein/peptide blocking ELISA were also used.

The solid phase ELISA was done by immobilizing protein on the plates (Immulon II plates, Dynatech Corp.) at a concentration of 1 µg/ml, diluted in a 0.2M carbonate bicarbonate solution, pH 9.2. Peptides were used at a concentration of 10 µg/ml dissolved in the same buffer. The wash buffer consisted of 1X PBS, with 0.05% Tween-20. The blocking buffer consisted of 2% BSA in the washing buffer. All of the antibodies were diluted in blocking buffer. The detection antibodies used were goat anti mouse, rabbit, or human Ig specific antibody, conjugated to horse radish peroxidase, (Boehringer Mannheim). These were used at a 1:12000 dilution, following manufacturer's specifications. The substrate used was 3,3',5,5' tetramethylbenzidine dihydrochloride (TMB Sigma), following manufacturer's specifications. The plates were developed for 15 minutes at room temperature in the dark. The reaction was stopped by adding 20 µl/well of 3M sulfuric acid, and read at OD 450 nm.

In the capture ELISA method, antibody diluted in carbonate bicarbonate buffer at 1 µg/ml is immobilized on the plate for two hours at 25° C. The samples are diluted in blocking buffer. All remaining steps were as described above.

The peptide blocking assay was performed by immobilizing one of the proteins of interest on the plate at a dilution of 1 µg/ml in carbonate bicarbonate. The peptides were dissolved in the blocking buffer at a dilution of 50 µg/ml, and added onto blocked wells. The second protein of interest is applied to these wells at a dilution of 1 µg/ml in the blocking buffer. The antibodies used from this point on are targeted toward the second protein, following the procedure described further above.

EXAMPLE 4

SDS-PAGE and Western Blot

SDS polyacrylamide gels were made following published procedures. Silver staining was performed using the Bio Rad Silver Stain Kit, following manufacturer's instructions.

Transfer of proteins from SDS-PAGE gels onto Immulon-P membranes (Millipore Corp.) was performed using the Bio Rad mini gel transfer system, following manufacturer's specifications. The blocking buffer used was 5% nonfat dry milk dissolved in the wash buffer (1x TBS supplemented with 0.05% Tween-20). The antibodies were diluted in the blocking buffer. The detection probe used was $I^{125}$ labeled protein G (Dupont-NEN), diluted to 2 µci/ml in the wash buffer.

EXAMPLE 5

Vpr Multi-step Western Blot System

Six 3×10 cells were washed twice in DPBS, and lysed in 200 µl of lysis buffer (100 mM NaCl, 50 mM Tris, pH 8.0, 0.5% Triton X-100, and the protease inhibitor cocktail described further above); incubated on ice for 10 minutes; and centrifuged at 12000 g for 6 minutes.

The triton soluble, as well as the triton insoluble fractions were run on 12% SDS-PAGE, and blotted on to an Immulon-P membrane (Millipore corp.). These membranes were blocked with 5% NFDM in 1x TBS (8 g NaCl, 0.2 g KCl, 3 g Tris base, in 1 liter, pH 7.4) with 0.05% tween-20. The membranes were incubated with either column purified recombinant vpr (approximately 50 mg/ml), or an identical preparation, except for the presence of the vpr protein. The following incubation was done using 808, a rabbit anti-vpr antisera, followed by Iodinated protein G. (Dupont-NEN). These filters were dried and exposed to film (KODAK X-AR) at −80° C., for at least 12 hrs, with an intensifying screen.

When the source of vpr used was tissue culture supernatant from chronically infected H9 cells, the following procedure was followed. H9 cells which had been chronically infected with HIV-I MN were grown to confluence. These supernatants were collected by centrifuging the cells at 1000 g for 10 minutes. The tissue culture supernatants were then diluted 1:10 in the lysis buffer described earlier, and supplemented with the above-mentioned protease inhibitors. This preparation was then employed in the step where recombinant vpr had been used before. The control used in these experiments was tissue culture supernatants from uninfected H9 cells, grown to the same level of confluence, and treated with the same lysis conditions.

EXAMPLE 6

Cell and Virus Culture

The following cell lines were obtained from the American Type Culture Collection: the TE 671 rhabdomyosarcoma line (ATCC HTB 139), as well as A673 rhabdomyosarcoma line (ATCC CRL 1598); the canine osteosarcoma cell line D17 (ATCC CCL 183) and the human osteosarcoma line HOS (ATCC CRL 1543); the glial blastoma line U373 (ATCC HTB17) and the Neuroblatoma line HTB10 (ATCC SK-N-MC). Two additional glial blastoma lines were provided by the MRC (HTB17 and HTB16). U87MG is a glial cell line obtained from the University of Pennsylvania Cell Center. RD rhabdomyosarcoma cells were obtained from another source. The t-lymphocytic cells used (H9, Supt-1) were obtained from the University of Pennsylvania Cell Center. THP-1 monocytic cells were obtained through the MRC. HL60 and U937 cells were obtained from another source; and KG-1 was obtained from still another source. The three monkey kidney cells used (BSC1, CV-1, and COS) were obtained from a different source. The murine NIH 3T3 was obtained from the ATCC; and the B cell hybridoma, NIH 183 was obtained from AIDS RR. The primary PBL as well as monocytes/macrophages were isolated from freshly drawn blood, from a normal individual, following published protocols. All of the adherent cells from the prior list were cultured in DMEM supplemented with 10% heat inactivated fetal calf serum, penicillin/streptomycin, 1-glutamine, Hepes and sodium pyruvate. The suspension cultures were cultured in RPMI 1640, supplemented with the same reagents. All these cells were cultured every four days, diluting them 1:10.

The virus containing supernatants were obtained from chronically infected H9 cells. These isolates (HIV-I MN, and HIV-I NL43) were obtained from the AIDS Reagent Repository program. The infected cells were grown to confluence, the cells were then removed by centrifugation and the supernatants diluted in lysis buffer described further above. Infection of H9 target cells was constantly monitored by measuring the levels of p24 in tissue culture supernatant.

EXAMPLE 7

Column Chromatography

The immunoaffinity columns used were constructed following published protocols. The desired antibodies were covalently coupled to protein A beads using DMP. These columns were loaded with the desired protein suspensions, and eluted with the strategy described further above.

A vpr-CnBr activated Sepharose column was also used. This column was made by dissolving the CnBr activated sepharose beads (Sigma) in 1 mM HCl, and allowed to swell for 10 minutes. These beads were washed with 20 bed volumes 0.1 M NaHCO(3), 0.5M NaCl, pH 8.3. Recombinant vpr was dissolved in the same wash buffer to a final concentration of 1 mg/ml, and incubated with the beads for 2 hours at room temperature. The coupled beads were blocked with 1M glycine in the same wash buffer, pH 8.5, for two hours at room temperature. This column was eluted with a preelution buffer composed of 10 mM sodium phosphate, pH 6.8, followed by the elution buffer; 100 mM glycine, pH 2.5. These fractions were neutralized with $\frac{1}{20}$ volume 1M sodium phosphate, pH 8.0.

EXAMPLE 8

Crosslinking of the Vpr/rip-1 Complexes

Vpr/rip-1 complexes were obtained using the column chromatography system described further above. Briefly, recombinant vpr was run on the column, followed by the Triton X-100 cell lysates, soluble fraction. These fractions were pooled and dialyzed against three changes of water. The resulting supernatant was lyophilized and resuspended in PBS to a tenth of the original volume. This solution was exposed to crosslinking agents. The crosslinkers used were DSS (Pierce), and DTSSP (Pierce). The latter is cleavable with reducing agents, DSS is a nonreversible crosslinker. Both of these agents needed to be dissolved at 50 mg/ml, in a 50% V/V water: DMSO mixture.

The resulting crosslinked fractions were run on 12% SDS-PAGE, either a reducing, or a non-reducing gel, and analyzed by the multi-step western blot method. Nonreducing gels were identical to their reducing counterparts, except for the presence of 2-beta mercaptoethanol and DTT in the loading buffer. These were denaturing gels, so they did contain SDS.

EXAMPLE 9

Mapping of the Vpr/rip-1 Interaction

The approach used to determine the sites of this interaction was a peptide-blocking ELISA system. Briefly, rbp-1 was immobilized on ELISA plates (Immulon II, Dynatech Corp.), dissolved at approximately 1 μg/ml in a 0.2M carbonate bicarbonate buffer, pH 9.2. The vpr peptides were dissolved in blocking buffer at 50 μg/ml, and incubated in the wells, using 50 μl/well. These are overlapping peptides, which span the entire length of the vpr molecule (obtained from the French AIDS Programme through the MRC repository, UK), the amino acid sequences of which are described in detail in Human Retroviruses and AIDS 1991, A Compilation and Analysis of Nucleic Acid and Amino Acid Sequences, G. Myers et al., eds., Division of AIDS, National Institute of Allergy and Infectious Diseases, published by Theoretical Biology and Biophysics Group T-10, Los Alamos National Laboratory, Los Alamos, N.M. Vpr was dissolved in blocking buffer at approximately 1 μg/ml. Different anti-vpr antibodies were used to detect the amount of vpr bound to the plates. Detection was accomplished by the use of a goat antiserum to mouse, or rabbit IgG, respectively, conjugated to horseradish, peroxidase.

In accordance with the above examples, it was found that the recombinant vpr protein migrated predominantly as a putative monomer at 15 KD on SDS PAGE. The silver staining, and the western blot also revealed the presence of a possible homodimer at 30 KD, at a lower concentration than the monomer. This protein was identical to native protein in its SDS-PAGE migration characteristics as well as in its antibody reactivity patterns.

Immunoaffinity chromatography was used as a means of obtaining protein which was >80% pure. It was observed that most of this purified protein migrates as a 15 KD band. Approximately 20% of the total protein present migrated as a high molecular weight compound, approximately 65 KD, which did not react with vpr specific antibodies in western blots.

Regarding recognition of rip-1 in cell lysate, the cell lysates were obtained by using different detergents in the lysis buffer. The detergents used were either Triton X-100, SDS, sodium deoxycholic acid, or a solution containing all three detergents (SDS, Triton X-100, and sodium deoxycholic acid). These lysis buffers were used to lyse 3×10(6) RD cells/sample.

The multi-step western blots showed a band at approximately 41 KD which hybridized in the Triton X-100 soluble portion, but not in the insoluble fraction. The same band hybridized in the other detergent lysates, but the subcellular localization could not be determined, as these detergents solubilized all cellular membranes. When native vpr was used in the multistep western blot system, instead of the recombinant protein described, the same 41 KD band hybridized. No additional bands were observed in this case either.

It was found that rip-1 expressed in an ubiquitous fashion in cell lines derived from T lymphocytes (H9, SupT-I), both cell lines, and primary cells, monocytes/macrophages (HL60, U937, THP-1, KG-1), from cell lines as well as primary cells, glial cells (HTB14, HTB10, U373), osteosarcoma cells (D17, HOS), rhabdomyosarcoma cells (RD, TE671, A673). All of these cells had rip-1 in their Triton X-100 soluble portions. The cell lines in which rip-1 was not detected were COS, BSC-1, CV-1, NIH 3T3, and a mouse derived B-cell hybridoma (NIH 183). Rip-1 was present in all the human cell lines that were screened, and in a canine osteosarcoma cell line (D17).

Regarding detection of rip-1 by column chromatography; when either RD lysates, or later on, U937 lysates were run on an anti-vpr column, following recombinant vpr, it was observed that a different elution profile than that which was obtained when vpr was run alone on the same column. Vpr will elute as one sharp peak, spanning about 5 fractions. Vpr followed by a cell lysate will yield a bimodal elution curve. These fractions will all have vpr activity, but this activity, when detected using a capture ELISA system, can sometimes block certain antibodies. The vpr detection/activity can ultimately be restored when a detection antibody which maps to a different region of vpr is used.

An analysis was done of the elution profiles, and their respective ELISA activities for different antibodies, in solid phase ELISA, and for different antibody combinations for a capture ELISA system. A mouse anti vpr (91–96) peptide was blocked in a capture ELISA system from the fractions in which vpr is associated with rbp-1. When a mouse anti-vpr (1–22) antibody is used in combination with a polyspecific rabbit antisera in a capture ELISA system, the presence of vpr is confirmed in both sets of fractions. This suggests that vpr is complexed with rip-1 such that it excludes the carboxy-terminus specific antibody from the reaction.

The multi-step western blot reactivity of these fractions showed a 41 KD band, in addition to vpr. This band correlates to that which was seen earlier with the whole cell lysates, and when run side by side to each other, appeared identical. Hence it was concluded that rip-1 had been isolated, bound to vpr in the column chromatography system.

With regard to isolation of rip-1, it was isolated by means of the vpr-CnBr activated Sepharose column. The Triton X-100 cellular lysates' soluble portion were incubated with this column for two hours at 4° C. This column was washed with 50 bed volumes of the adequate wash buffer, and eluted. The samples were analyzed by SDS-PAGE, silver staining, and western blot, as well as by their ability to bind vpr in ELISA. The column initially yielded some vpr in the first four fractions, which coeluted with rip-1. Upon additional strippings, the resulting fractions only contained rip-1. This was the source for >95% pure rip-1 used in the mapping studies described further above and commented on further below.

With regard to crosslinking of the vpr/rip-1 complexes, two crosslinking reagents were used, a cleavable (DSS), and a noncleavable (DTSSP) one. The noncleavable crosslinker, DSS, is a homobifunctional agent, which will covalently couple proteins found at a close proximity. DTSSP is a thiol cleavable crosslinker. These two chemical crosslinking agents are identical in every aspect other than their reversibility. A 58 KD band was detected on SDS-PAGE, by silver staining. This molecule reacted with anti-vpr antisera as well as in the multi step western blot system, like vpr, and rip-1 would react, individually. The DSS crosslinked complexes were run side by side with the DTSSP crosslinked complexes, to the undisturbed column fractions. These were run on both, reducing and nonreducing SDS-PAGE. The purpose of this was to observe the separation of the crosslinked complexes into its specific components, vpr and rip-1. Analysis showed a gel in which the 58 KD band was observed in the nonreducing gel, for both crosslinkers, whereas in the reducing gel, it could be seen that the 58 KD band was in the DSS lane only, and the 41 KD plus the 15 KD band, corresponding to vpr and rip-1, were in the DTSSP lane, as could be seen in the unaltered column fraction lane.

With regard to mapping of the vpr/rip-1 interaction, there was obtained 14 overlapping peptides from the French AIDS research program. A peptide blocking ELISA system was used in order to determine the site, on the vpr molecule, in which rip-1 binds vpr. The area of this interaction was resolved to amino acids x to y. This is consistent with the pattern of antibody blocking of this interaction, as the m. anti p2 antibody blocked this interaction; but other antibodies, raised against the amino, and the carboxy termini, did not give this result.

With regard to rip-1 translocation to the nucleus in response to vpr stimuli, U937 cells were used in order to explore the effects of vpr on rip-1 in vivo. These myeloid cells were either infected with HIV-1 NL43, or infected with a vpr deleted HIV-1 NL43; in the presence, or absence of recombinant vpr protein. U937 cells were also exposed to PMA, or to recombinant, soluble vpr alone. The effects of vpr on the cellular localization of rip-1 were assessed with the multistep western blot system. In addition, the infections were monitored by measuring the supernatant levels of gag p24. These experiments were carried out as a time course, collecting samples at 12, 24, 48, 72, 96, and 120 hours postinfection.

In each case in which the cells were exposed to soluble vpr, the multistep western blot showed vpr in the cytoplasmic cellular fraction at 12 hrs, and subsequently in both, the cellular and nuclear fractions. Rip-2 was always seen colocalizing with vpr. It was also observed that a translocation of vpr and of rip-1 from the cytoplasmic fractions to the nuclear fractions occurred. The phorbol ester PMA did not induce this translocation, and neither did a vpr deleted HIV virus. The translocation effect was rescued in the case of the vpr deleted virus upon the addition of recombinant vpr to the infected cultures. Other methods in addition to multistep western blot may be employed to demonstrate this nuclear colocalization of vpr and rip-1, such as the ELISA techniques described herein.

The levels of p24, which reflect a productive HIV infection, were measured. There was detected p24 in the supernatants of the HIV-I NL43 infected cultures at 96 hours postinfection. There was no detection of any p24 in the supernatants of the vpr deleted HIV NL43 infected cultures in the 120 hours that were analyzed. In addition, there was no detection of any p24 in the culture supernatants of the cells which were exposed to PMA, or to recombinant vpr only. The cultures which were exposed to both, recombinant vpr, and the vpr deleted virus, showed p24 at 48 hours postinfection. In addition, these cultures showed the same rip-1 translocation profile as the cultures exposed to recombinant vpr only. In all the cases in which p24 was detected in the supernatant, the translocation of rip-1 from the cytoplasm to the nucleus was observed up to 24 hours beforehand.

What is claimed is:

1. An in vitro method of identifying a compound which is capable of preventing HIV-1 Vpr from forming a complex with Rip-1 comprising the following steps:
   a) contacting Vpr and Rip-1 in the presence of said compound;
   b) determining the level of Vpr/Rip-1 complex formation;
   c) comparing the level of Vpr/Rip-1 complex formation in step (b) to the level of Vpr/Rip-1 binding that occurs in the absence of said test compound.

2. The method of claim 1 wherein said level of Vpr/Rip-1 complex formation is determined by immunoassay.

3. An in vitro method of identifying a compound which is capable of preventing HIV-1 Vpr from forming a complex with Rip-1 comprising the following steps:
   a) immobilizing Rip-1 to a solid support;
   b) contacting said immobilized Rip-1 with Vpr and a test compound;
   c) measuring Vpr binding to immobilized Rip-1 through the administration of Vpr-specific antibodies; and,
   d) comparing the level of Vpr/Rip-1 binding in step (c) to the level of Vpr/Rip-1 binding that occurs in the absence of said test compound.

4. An in vitro method of identifying a compound which is capable of preventing HIV-1 Vpr from forming a complex with Rip-1 comprising the following steps:
   a) immobilizing Vpr to a solid support;
   b) contacting said immobilized Vpr with Rip-1 and a test compound;
   c) measuring Rip-1 binding to immobilized Vpr through the administration of Rip-1-specific antibodies; and,
   d) comparing the level of Vpr/Rip-1 binding in step (c) to the level of Vpr/Rip-1 binding that occurs in the absence of said test compound.

5. An in vitro method for the identification of compounds capable of inhibiting HIV-1 Vpr from forming a complex with Rip-1, said method comprising the following steps:
   a) contacting a culture of HIV-1-infected cells with a test compound;
   b) determining the level of Vpr/Rip-1 binding in said HIV-1infected cells; and,
   c) comparing the level of Vpr/Rip-1 binding in step (b) to the level of Vpr/Rip-1 binding that occurs in HIV-1-infected cells cultured in the absence of said test compound.

6. An in vitro method for the identification of compounds capable of inhibiting HIV-1 viral replication through the abrogation of HIV-1Vpr/Rip-1 complex cytoplasmic to nuclear translocation, said method comprising the following steps:
   a) contacting a culture of HIV-1-infected cells with a test compound;
   b) determining the level of cytoplasmic to nuclear translocation of HIV-1 Vpr/Rip-1 complexes; and,
   c) comparing the level of cytoplasmic to nuclear translocation of HIV-1 Vpr/Rip-1 complexes in the presence of said test compound to the level of cytoplasmic to nuclear translocation of HIV-1 Vpr/Rip-1 complexes that occurs in HIV-1-infected cells cultured in the absence of said test compound.

7. A method according to claim 6 further comprising the following steps:
   d) determining the level of p24 antigen produced in HIV-1 infected cells cultured in the presence of said test compound;
   e) comparing the level of p24 antigen produced in HIV-1-infected cells cultured in the presence of said test compound to the level of p24 antigen produced by HIV-1-infected cells cultured in the absence of said test compound;
wherein said comparison results in the identification of compounds capable of inhibiting HIV-1 viral replication.

8. An in vitro method for the identification of glucocorticoid receptor antagonists capable of inhibiting HIV-1 Vpr from forming a complex with Rip-1, said method comprising the following steps:
   a) contacting a culture of HIV-1-infected cells with a glucocorticoid receptor antagonist;
   b) determining the level of Vpr/Rip-1 binding in said HIV-1 infected cells; and, c) comparing the level of Vpr/Rip-1 binding in step (b) to the level of Vpr/Rip-1 binding that occurs in HIV-1-infected cells cultured in the absence of said test compound.

9. An in vitro method for the identification of glucocorticoid receptor antagonists capable of inhibiting HIV-1 viral replication through the abrogation of HIV-1 Vpr/Rip-1 complex cytoplasmic to nuclear translocation, said method comprising the following steps:

a) contacting a culture of HIV-1-infected cells with a glucocorticoid receptor antagonist;

b) determining the level of cytoplasmic to nuclear translocation of HIV-1 Vpr/Rip-1 complexes; and, c) comparing the level of cytoplasmic to nuclear translocation of HIV-1 Vpr/Rip-1 complexes in the presence of said test compound to the level of cytoplasmic to nuclear translocation of HIV-1 Vpr/Rip1 complexes that occurs in HIV-1-infected cells cultured in the absence of said test compound.

* * * * *

UNITED STATES PATENT AND TRADEMARK OFFICE
CERTIFICATE OF CORRECTION

PATENT NO. : 5,639,598

DATED : June 17, 1997

INVENTOR(S) : David B. Weiner et al

Page 1 of 2

It is certified that error appears in the above-indentified patent and that said Letters Patent is hereby corrected as shown below:

Col. 3, line 40, "replicatire" should be --replicative--.

Col. 4, line 3, "replicatire" should be --replicative--.

Col. 4, line 43, "replicatire" should be --replicative--.

Col. 5, line 17, "replicatire" should be --replicative--.

Col. 5, line 32, "replicatire" should be --replicative--.

Col. 5, line 48, "delected" should be --deleted--.

Col. 6, line 41, "determing" should be --determining--.

Col. 7, line 57, "gtucocorticoid" should be --glucocorticoid--

Col. 9, line 17, "agohist" should be --agonist--.

Col. 12, line 21, "may be used for production in" is repeated twice

UNITED STATES PATENT AND TRADEMARK OFFICE
CERTIFICATE OF CORRECTION

PATENT NO. : 5,639,598
DATED : June 17, 1997
INVENTOR(S) : David B. Weiner et al It is certified that error appears in the above-indentified patent and that said Letters Patent is hereby corrected as shown below:

Col. 15, line 57, "quantirate" should be --quantitate--.

Signed and Sealed this

Twenty-fifth Day of November, 1997

BRUCE LEHMAN

Attest:

Attesting Officer

Commissioner of Patents and Trademarks